US012344682B2

(12) United States Patent
Arnoni et al.

(10) Patent No.: US 12,344,682 B2
(45) Date of Patent: Jul. 1, 2025

(54) MALTODEXTRIN AND PROCESS OF MAKING SAME

(71) Applicant: CORN PRODUCTS DEVELOPMENT, INC., Westchester, IL (US)

(72) Inventors: Laercio Arnoni, Bridgewater, NJ (US); Jose Bertoli, Bridgewater, NJ (US); Walter Yamamoto, Bridgewater, NJ (US)

( * ) Notice: Subject to any disclaimer, the term of this patent is extended or adjusted under 35 U.S.C. 154(b) by 0 days.

(21) Appl. No.: 18/299,303

(22) Filed: Apr. 12, 2023

(65) Prior Publication Data

US 2023/0242680 A1 Aug. 3, 2023

Related U.S. Application Data

(62) Division of application No. 16/639,425, filed as application No. PCT/US2018/046701 on Aug. 14, 2018, now Pat. No. 11,655,311.

(60) Provisional application No. 62/545,530, filed on Aug. 15, 2017.

(51) Int. Cl.
| | | |
|---|---|---|
| C08B 30/18 | (2006.01) | |
| C12N 9/26 | (2006.01) | |
| C12N 9/44 | (2006.01) | |
| C12P 19/04 | (2006.01) | |
| C12P 19/16 | (2006.01) | |
| C12P 19/22 | (2006.01) | |

(52) U.S. Cl.
CPC ............ *C08B 30/18* (2013.01); *C12N 9/2414* (2013.01); *C12N 9/2457* (2013.01); *C12P 19/04* (2013.01); *C12P 19/16* (2013.01); *C12P 19/22* (2013.01)

(58) Field of Classification Search
CPC ................................ C12P 19/04; C12P 19/08
See application file for complete search history.

(56) References Cited

U.S. PATENT DOCUMENTS

| | | | |
|---|---|---|---|
| 3,974,033 | A | 8/1976 | Harjes et al. |
| 3,974,034 | A | 8/1976 | Horn et al. |
| 5,853,487 | A | 12/1998 | Tang et al. |
| 2013/0112192 | A1* | 5/2013 | Fosdick .................. C12P 19/04 127/30 |
| 2018/0319900 | A1 | 11/2018 | Ibert et al. |
| 2021/0032668 | A1 | 2/2021 | Arnoni et al. |

FOREIGN PATENT DOCUMENTS

| | | |
|---|---|---|
| CN | 102766666 A | 11/2012 |
| EP | 1435390 A1 | 7/2004 |
| WO | 03/018766 | 3/2003 |
| WO | 2006047176 A1 | 5/2006 |
| WO | 2017/098191 | 6/2017 |

OTHER PUBLICATIONS

H.Sreenath, et al., "Effect of Pullulanase and A-Amylase on Hydrolysis of Waxy Corn Starch", VCH Verlagsgesellschaft mBH, D-6940 Weinheim, 1990 pp. 482-486.
N.Castro, et al., "Influence of De-Value on the Physicochemical Properties of Maltodextrin for Melt Extrusion Processes", Journal Carbohydrate Polymers 144 (2016) pp. 464-473.
Hll et al., "Pulluanase role in Starch Hydrolysis and Potential Industrial Applications" Enzyme Research vol. 2012, Article ID 921362, 14 pages (year 2012).
Mobini-Dehkordi et al., "Application of alpha-amylase in biotechnology", Journal of Biology an todays world, vol. 1, Issue 1, pp. 39-50 (year 2012).
Deffenbaugh et al., "Comparison of Starch Pasting Properties in the Brabender Viscoamylograph and the Rapid Visco Analyzer" Cereal Chemistry, vol. 66, No. 6, pp. 493-499 (Year 1989).
Goode et al., "Application of rapid visco analyser as a rheological tool for the characterization of mash viscosity as affected by the level of barley adjunct" J Inst Brew, vol. 11, No. 2, pp. 165-167 (Year 2002).
Balet et al., "Rapid visco analyser (RVA) as a tool for measuring starch-related physiochemical properties in cereals: a review", Food Analytical Methods, vol. 12, pp. 2344-2360 (Year 2019).
Van der Sman et al., "Scaling relations in rheology of concentrated starches and maltodextrins", Food Hydrocolloids, vol. 124, pp. 1-10, https://doi.org/10.1016/j.foodhyd.2021.107306 (Year 2022).
Dong Soon Suh et al., "Comparison of Starch Pasting Properties at Various Cooking Conditions Using the Micro Visco-Amylo-Graph and the Rapid Visco Analyser", Cereal Chemistry, vol. 80, No. 6, Nov. 2003, pp. 745-749.
Tur et al., "Charakterystyka Maltodekstryn Otrzymanych ZE Skrobi Ziemniaczanej Przy Uzyciu Preparatow Amylolitycznych" Zywnosc Nauka Technologia Jakosc vol. 4(41) pp. 79-94 (Year 2004).

* cited by examiner

*Primary Examiner* — Eric Olson

(57) ABSTRACT

This specification discloses process for obtaining maltodextrin having DE between 17 and 19.9 and the maltodextrins obtained from the process. The disclosed maltodextrins can be provided as a powder or in shelf stable liquid form. The disclose maltodextrins have a polysaccharide profile similar to those observed for prior art maltodextrins, but make maltodextrin solutions having a high solids content, but reduced viscosity compared to prior art maltodextrins, on equivalent solids-in-solution basis. The process combines adds an alpha-amylase and a pullulanase enzyme to a polysaccharide mixture during a saccharification step. The disclosed maltodextrins make solutions at 50° C. and greater than 65% on a solids dry solids basis having a viscosity between 5,000 and 12,000 cP and having a water activity of less than 0.80.

11 Claims, 1 Drawing Sheet

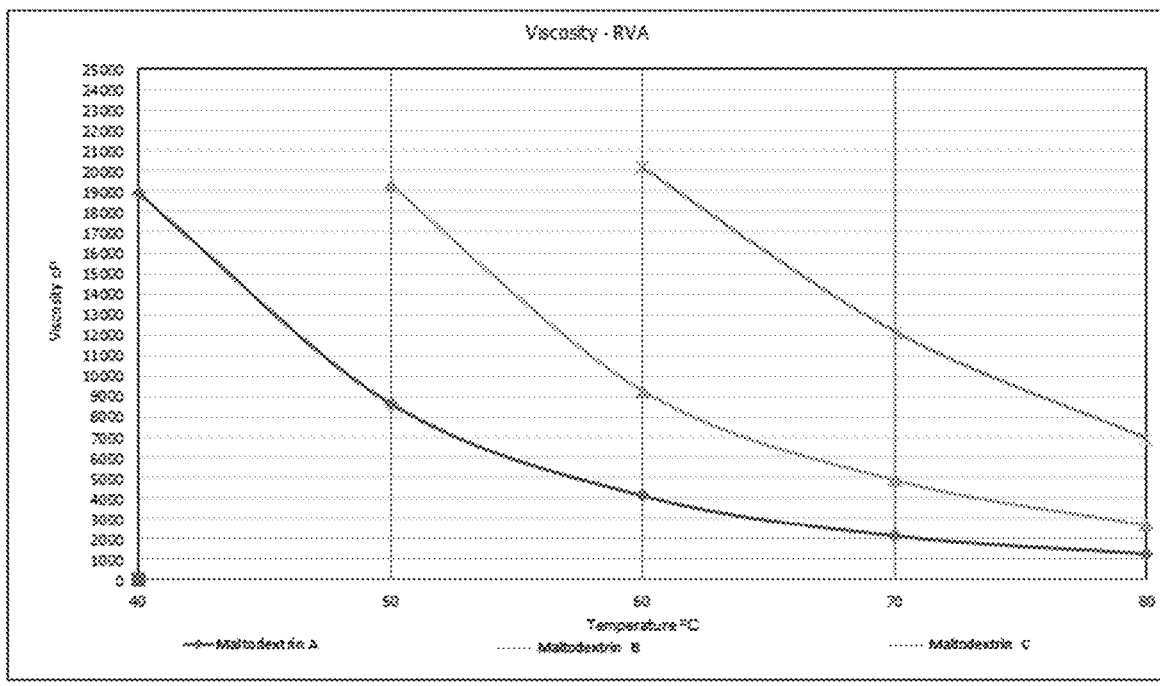
♦ Maltodextrin A – an illustrative embodiment of the disclosed maltodextrin having DE between 17 and 19.9.
▲ Maltodextrin B – a commercially available maltodextrin having DE between 17 and 19.9.
X  Maltodextrin C – a commercially a commercially available maltodextrin having DE between 17 and 19.9.

MALTODEXTRIN AND PROCESS OF MAKING SAME

CROSS REFERENCE TO RELATED APPLICATIONS

This application is a divisional of application Ser. No. 16/639,425, filed on Feb. 14, 2020, which is now allowed, which is a 35 USC § 371 of International Application No. PCT/US2018/046701, filed Aug. 14, 2018, which claims priority to U.S. Provisional Application Ser. No. 62/545,530, filed on Aug. 15, 2017, which are all hereby incorporated by reference herein in their entirety.

This specification discloses a process for obtaining a maltodextrin having a dextrose equivalent between 17.0 and 19.9. The maltodextrins made according to the process have different physical properties than those of the prior art, which enhance the usefulness of the maltodextrins.

Maltodextrins are widely used. For example they are used as bulking agents, drying agents, tableting agents, film forming agents and fat replacers. They can also be used to control viscosity, osmolarity, and sweetness of products. They can also be used to prevent crystallization in products. And there are other known uses. Solutions made from prior art maltodextrins have high viscosity (greater than about 15,000 cP at 50° C.), at high solids content, (greater than 65% solids by weight of the solution on a dry solids basis). The high viscosity solution presents several problems. For example, it has a short shelf-life (between 2 and 5 days) due to high water activity (higher than 0.9) and consequent microbiological growth. Also the solution is very sticky, which, along with the high viscosity, makes the solution hard to process because it is difficult to load and process in typical drying equipment. So because of their poor shelf life, maltodextrins are typically sold in powdered form. But because of their poor processing characteristics, maltodextrin powders are typically obtained from low solids content solutions, which increases water usage, time and energy needed to obtain maltodextrin powders.

An embodiment of the process for making maltodextrin from starch, comprises applying a liquefaction step comprising adding either an acid or an enzyme to an aqueous starch mixture in sufficient amount to hydrolyze the starch to form a mixture comprising polysaccharides; and applying a saccharification step comprising adding an alpha-amylase and a pullulanase to hydrolyze the polysaccharides in the mixture to obtain maltodextrin. The enzymatic liquefaction step may comprise a single heating/enzyme dosage or double heating/enzyme dosages (DEDH—Dual Enzyme Dual Heating).

An embodiment of the powdered maltodextrin comprises a dextrose equivalent between 17 and 19.9; and a distribution of polysaccharides comprising less than 5% by weight polysaccharides having a degree of polymerization of 1 ("DP"1—i.e. a monosaccharide), between 4% and 10% by weight polysaccharides having DP2, between 9% and 14% by weight polysaccharides having DP3, and between 75% and 82% by weight polysaccharides having DP4+(at least four glucosidic units).

The disclosed maltodextrins can also be used to make maltodextrin solutions. In one embodiment, a maltodextrin solution comprising greater than 65% by weight maltodextrin solids that has a viscosity of between 5,000 and 12,000 cP at 50° C. In another embodiment a maltodextrin solution comprising greater than 65% by weight maltodextrin solids has a water activity of less than 0.85. In still another embodiment maltodextrin solutions comprising greater than 65% by weight maltodextrin have a shelf life of greater than 5 days.

FIGURES

FIG. 1 graphically compares the viscosity of maltodextrin solutions (78.8% maltodextrins, dry weight) using an illustrative embodiment of the disclosed maltodextrins with solutions (78.8% maltodextrins, dry weight) using prior art maltodextrins.

Within this specification, polysaccharides refer generally to the mixture of glucose molecules and glucose polymers derived from starch hydrolysis by the disclosed processes. Accordingly, polysaccharides include starch derivatives having a degree of polymerization of 1 (DP1)—i.e. glucose—through DPn; more specifically, the term polysaccharide is used as a short hand to refer to a collection of molecules that may be more accurately described as including glucose, dextrin, maltodextrins, and/or oligosaccharides.

Embodiments of the disclosed processes may be used to make maltodextrins of any dextrose equivalences. In embodiments the process is a process for making a maltodextrin having a DE between 17 and 19.9. In embodiments, the process comprises a liquefaction step and a saccharification step. In an embodiment an aqueous starch mixture is subjected to a liquefaction step that uses a suitable acid to make a mixture comprising polysaccharides. In such embodiments, the acid is any acid typically used in starch processing, for example, but not limited to sulfuric acid or hydrochloric acid. In a further embodiment the acid is added in an amount sufficient for the pH of the mixture to be between 1.8 and 2.2. In another embodiment acid is added to the aqueous starch mixture in the amount of from 0.01 to 0.04 meq/mL. In still another embodiment acid hydrolysis is run at temperatures ranging from 135° C. to 145° C.

In yet another embodiment, liquefaction uses an enzyme suitable for making the mixture comprising polysaccharides. In such embodiments, the enzyme is any enzyme suitable for hydrolyzing the 1,4 glucosidic bonds within the aqueous starch mixture, for example an alpha amylase. In a further embodiment, alpha-amylase is mixed with the aqueous starch mixture in the amount of from 0.05 to 0.80 g of enzyme per kg of starch on a dry basis. In yet further embodiments the reaction runs at temperatures ranging from 90° C. to 110° C. In still other embodiments the pH ranges varies from 6.0 to 7.0. In a still further embodiment, liquefaction uses an alpha-amylase that is thermostable at temperatures used to gelatinize starch (e.g. greater than 100° C., and typically between 100° C. and 160° C.). The enzymatic liquefaction step may be run once, or more than once in order to ensure that the starch is sufficiently gelatinized before it subjected to saccharification. In one embodiment the liquefaction comprises a using a single does, and single heating cycle (a "single heating/enzyme dosage liquefaction"). In another embodiment the liquefaction step uses twice the dose of enzyme added during the course heating steps (a "double heating/enzyme dosages or "DEDH"). In an embodiment the DEDH is done by running two complete liquefaction cycles sequentially. In another embodiment the DEDH adds twice the dose over enzyme over a single heating cycle, but which is run for twice the amount of time as for a single heating cycle.

In further embodiments the liquefaction step, whether using acid or enzyme, is run until the mixture comprising polysaccharides has dextrose equivalent ranging from 13 to 17.

In embodiments the mixture comprising polysaccharides is subjected to a saccharification step using two or more enzymes capable of hydrolyzing the 1,4 and 1,6 glucosidic bonds of the polysaccharides in the polysaccharide mixture. In another embodiment the enzymes are pullulanase and alpha-amylase. In still another embodiment, alpha-amylase is mixed with the polysaccharide mixture in an amount that varies from 0.01 to 0.05 g of alpha-amylase per kg of starch. In yet another embodiment, pullulanase is mixed with the polysaccharide mixture in an amount of between 0.30 to 0.60 g of pullulanase per kg of starch. In still another embodiment the temperature range for saccharification is from 40° C. to 60° C. In a further embodiment, the pH varies from 4.0 to 7.5. In an even further embodiment the saccharification time ranges from 2 hours to 12 hours.

In other embodiments the alpha-amylase of the liquefaction step may be used as part of the saccharification step, or the liquefaction step may be stopped by deactivating the enzyme, for example, by increasing the temperature or changing the pH of the mixture comprising polysaccharides. In still yet another embodiment the alpha-amylase may be a different alpha-amylase than is used in the liquefaction step.

In embodiment the alpha amylase is selected to more likely digest internal 1,4 glucosidic linkages, a so called endo-alpha-amylase. In yet another embodiment the alpha-amylase is selected to randomly digest 1,4 glucosidic linkages. In even another embodiment, the alpha-amylase may be a commercially obtainable alpha-amylase, for example, including, but not limited to Termamyl 120L, BAN 480 L, Liquozyme Supra, Spezyme Fred or the like. In still another embodiment the pullulanase is a commercially available pullulanase, including, for example, but not limited to Promozyme D 2, Optimax L 1000, Promozyme 400, or the like.

In embodiments the maltodextrin solution made during the saccharification step may be further purified, for example, using centrifugation or vacuum filter to separate the maltodextrins from proteins in the mixture. As another example, the maltodextrins may be purified to remove colors, odors, or tastes, for example by using carbon filtration or resins.

In embodiments the purified solution can be concentrated and provided as a high solids content maltodextrin solution having at least 65% maltodextrin by weight (dry basis), or at least 70% maltodextrin by weight (dry basis), or at least 75% maltodextrin by weight (dry basis), or at least about 78% maltodextrin by weight (dry basis), or at least about 80% maltodextrin by weight (dry basis), or between about 65% and about 85% maltodextrin by weight (dry basis). In other embodiments the purified solution can be dried to recover maltodextrin powders using any process known in the industry for concentrating and recovering maltodextrins from solution, including but not limited to roller chillers or spray driers. In still other embodiments the powdered maltodextrin may be dissolved in an aqueous solution to make a high-solids content maltodextrin solution having at least 65% maltodextrin by weight (dry basis), or at least 70% maltodextrin by weight (dry basis), or at least 75% maltodextrin by weight (dry basis), or at least about 78% maltodextrin by weight (dry basis), or at least about 80% maltodextrin by weight (dry basis), or between about 65% and about 85% maltodextrin by weight (dry basis).

In embodiments, the base starch for use in the process may be from various sources, for example, but not limited to corn, cassava, potato, rice, wheat, pulses and other sources, as well as waxy or high amylose variants of the preceding starches. In other embodiments, the starting material may also be made from mixtures of one or more starches.

In embodiments maltodextrin powders have a polysaccharide distribution (DP1, DP2, DP3, and DP4+) similar to those of the prior art. In another embodiment, the polysaccharides of the maltodextrin will have various degrees of polymerization (DP). In yet another embodiment the distribution will comprise less than 5% polysaccharides having DP1 (i.e. a monosaccharide), between 4% and 10% polysaccharides having DP2, between 9% and 14% polysaccharides having DP3, and the between 75% and 82% polysaccharides having DP4+—i.e. having four or more glucosidic units.

In embodiments solutions comprising the disclosed maltodextrins have lower viscosity (on an equivalent solids basis) than prior art maltodextrin solutions. In such embodiments the solutions comprising maltodextrin have a viscosity of between 5,000 and 12,000 cP, or between 7,000 and 10,000 cP. In another embodiment solutions comprising maltodextrin having at least 65% maltodextrin by weight (dry basis), or at least 70% maltodextrin by weight (dry basis), or at least 75% maltodextrin by weight (dry basis), or at least about 78% maltodextrin by weight (dry basis), or at least about 80% maltodextrin by weight (dry basis), or between about 65% and 85% maltodextrin by weight (dry basis) have a viscosity of between 5,000 and 12,000 cP, or between 7,000 and 10,000 cP at 50° C. In still another embodiment, solutions comprising maltodextrin have low water activity compared to solutions using prior art maltodextrins (on an equivalent solids basis.) The reduced viscosity advantageously facilitates processing of solutions having a solids concentration of about 75% to 85% because lower viscosity, less sticky solutions are more easily handled by standard drying equipment such as spray dryers or chill rollers at higher concentrations than prior art maltodextrins. Additionally, high solids concentration solutions beneficially reduce the amount of water used, and beneficially increase the rate at which solids can be recovered.

In such embodiments the solutions comprising maltodextrin have a water activity of less than 0.85, or less than 0.75, or less than 0.70, or between 0.70 and 0.75. In yet another embodiment, a maltodextrin solution having 80% by weight maltodextrin (dry basis) has a water activity of less than about 0.85, or 0.75, or 0.70, or 0.70 and 0.75. In a further embodiment, solutions comprising maltodextrin made have less microbiological growth and so longer shelf life. In embodiments solutions comprising between 70% and 85% solids and having a water activity of between about 0.85 and 0.70 are shelf stable against microbiological degradation for at more than one week, or more than two weeks, or more than one month, or more than two months, or up to about 2 months.

Without being bound by theory, Applicants believe that the weight distribution of the maltodextrins having DP4+ is smaller than for prior art maltodextrins, and maltodextrins made by prior art processes, which contributes to the improved water activity and viscosity of the disclosed high solid content maltodextrin solutions.

Within this specification the recitation of particular ranges includes all subranges within the broader range.

The maltodextrins and process for making maltodextrins disclosed in this specification are further described by the examples below, which provide illustrative embodiments. The examples are not intended to be limiting in any way and a person of ordinary skill in the art would understand that disclosed parameters can be varied and still be within the spirit of the invention and the scope of the claims.

Table 1 compares the viscosities of solutions made using an embodiment of the disclosed maltodextrins and commercially available maltodextrins. Solutions had solids concentration of 78.8%. Samples were measured at the given temperatures using a rapid visco analyzer. The same results are also shown in FIG. 1.

TABLE 1

RVA Viscosity (cP)

| Temperature | Maltodextrin A (Test Sample) | Maltodextrin B (Commercial Sample) | Maltodextrin (Commercial sample) |
|---|---|---|---|
| 40° C. | 18,900 | Cannot be measured | Cannot be measured |
| 50° C. | 8,600 | 19,300 | Cannot be measured |
| 60° C. | 4,100 | 9,300 | 20,200 |
| 70° C. | 2,200 | 4,900 | 12,100 |
| 80° C. | 1,300 | 2,700 | 6,900 |

Table 2 below shows the water activity of an illustrative solution made from the disclosed maltodextrins. Increased water activity correlates with increased microbiological development and, consequently, reduced shelf-life.

In one embodiment, the water activity of an 80% solids solution is less than 0.80 and, in another embodiment, less than 0.70.

TABLE 2

Water activity ($a_w$)

| Solids (%) | Water activity ($a_w$) |
|---|---|
| 59.7 | 0.942 |
| 65.4 | 0.922 |
| 70.1 | 0.893 |
| 74.3 | 0.855 |
| 77.2 | 0.847 |
| 78.1 | 0.838 |
| 79.2 | 0.783 |
| 82.6 | 0.740 |

The invention claimed is:

1. A process for making maltodextrin from starch, comprising:
   applying a liquefaction step comprising adding an acid or an enzyme to an aqueous starch mixture in sufficient amount to hydrolyze the starch to obtain a mixture comprising polysaccharides; and
   applying a saccharification step comprising adding an alpha-amylase and a pullulanase to sufficiently hydrolyze the polysaccharides in the mixture to obtain maltodextrin;
   wherein the maltodextrin, when in powdered form, has a DE from 17 to 19.9.
   wherein the maltodextrin, when in powdered form, has a distribution of polysaccharides comprising less than 5% by weight polysaccharides having DP1, between 4% and 10% by weight polysaccharides having DP2, between 9% and 14% by weight polysaccharides having DP3, and between 75% and 82% by weight polysaccharides having DP4+ of at least 4.

2. The process of claim 1 wherein the liquefaction step comprises adding an acid in sufficient amount such that the pH of the aqueous starch mixture is between 1.8 and 2.2.

3. The process of claim 1 wherein the liquefaction step comprises adding an alpha-amylase in a concentration ranging from 0.05 to 0.80 g of enzyme per kg of starch on a dry basis, and hydrolyzing the starch in the aqueous starch mixture at a temperature between 90°° C. and 110° C. and at a pH ranging from 6.0 to 7.0.

4. The process of claim 1 wherein the liquefaction step runs until the polysaccharide mixture has a DE ranging from 13 to 17.

5. The process of claim 1 further comprising, during the saccharification step, adding to the polysaccharide mixture the alpha-amylase in an amount ranging from 0.01 to 0.05 g per kg of starch on a dry basis and the pullulanase in an amount ranging from 0.30 to 0.60 g per kg of starch on a dry basis, and hydrolyzing the polysaccharides in the mixture at a temperature ranging from 40° C. to 60° C. and at a pH ranging from 4.0 to 7.5, for a time of between 2 and 12 hours.

6. The process of claim 1 comprising, during the saccharification step, adding to the polysaccharide mixture the alpha-amylase in an amount ranging from 0.01 to 0.05 g per kg of starch on a dry basis and the pullulanase in an amount ranging from 0.30 to 0.60 g per kg of starch on a dry basis, and hydrolyzing the polysaccharides in the mixture at a temperature ranging from 40° C. to 60° C. and at a pH ranging from 4.0 to 7.5, for a time of between 2 and 7 hours.

7. The process of claim 1 wherein the liquefaction step is a single dosage liquefaction.

8. The process of claim 1 wherein the liquefaction step is a double dosages liquefaction.

9. The process of claim 1 wherein a maltodextrin solution comprising at least 78% by weight of the maltodextrin on a dry solids basis has a viscosity of between 5,000 and 12,000 cP as measured at 50° C. using a rapid visco analyzer.

10. The process of claim 1 wherein the starch is selected from the group consisting of: corn starch, wheat starch, tapioca starch, potato starch, sweet potato starch, sago starch, barley starch, rice starch, heat/acid treated starch, dextrin, pearl starch, waxy corn starch, sorghum starch, high amylose corn starch and liquid dextrose of high solid content and combinations thereof.

11. The process of claim 1 wherein the starch is a chemically unmodified starch.

* * * * *